United States Patent
Nakamura et al.

(10) Patent No.: US 12,103,217 B2
(45) Date of Patent: Oct. 1, 2024

(54) STRETCHABLE SHEET MANUFACTURING METHOD

(71) Applicant: ZUIKO CORPORATION, Settu (JP)

(72) Inventors: Hideyuki Nakamura, Settu (JP); Miwa Koshijima, Settu (JP)

(73) Assignee: ZUIKO CORPORATION, Settu (JP)

( * ) Notice: Subject to any disclaimer, the term of this patent is extended or adjusted under 35 U.S.C. 154(b) by 144 days.

(21) Appl. No.: 16/967,025

(22) PCT Filed: Dec. 14, 2018

(86) PCT No.: PCT/JP2018/046144
§ 371 (c)(1),
(2) Date: Aug. 3, 2020

(87) PCT Pub. No.: WO2019/155765
PCT Pub. Date: Aug. 15, 2019

(65) Prior Publication Data
US 2021/0031428 A1     Feb. 4, 2021

(30) Foreign Application Priority Data

Feb. 6, 2018 (JP) .................................. 2018-019662

(51) Int. Cl.
*B29C 48/00* (2019.01)
*A61F 13/00* (2024.01)
(Continued)

(52) U.S. Cl.
CPC ...... *B29C 48/305* (2019.02); *A61F 13/15682* (2013.01); *A61F 13/49* (2013.01);
(Continued)

(58) Field of Classification Search
CPC ....... B29C 48/00; B29C 48/30; B29C 48/305; A61F 13/00; A61F 13/10; A61F 13/15;
(Continued)

(56) References Cited

U.S. PATENT DOCUMENTS

2010/0104830 A1   4/2010   Jaeger et al.
2010/0114051 A1   5/2010   Saito et al.
(Continued)

FOREIGN PATENT DOCUMENTS

EP    1104692 A2    6/2001
EP    1 900 512 A1  3/2008
(Continued)

OTHER PUBLICATIONS

PCT/ISA/210, "International Search Report for International Application No. PCT/JP2018/046144," Mar. 12, 2019.
(Continued)

*Primary Examiner* — Michael N Orlando
*Assistant Examiner* — Joshel Rivera
(74) *Attorney, Agent, or Firm* — HAUPTMAN HAM, LLP

(57) ABSTRACT

In the present invention, an elastic resin material having a thermoplastic elastic resin is extruded into a sheet shape on a die and made to have a thickness that varies along the width direction, and then is cooled, to a temperature in which the elastic resin material elastically deforms, to form a sheet body that varies in thickness along the width direction, and a stretchable sheet is formed by laminating and joining base sheets. The sheet body includes at least two first and second regions adjacent to each other in the width direction, and the thicknesses of the second regions are greater than that of the first regions. In a wearable article, the stretchable sheet is disposed so that at least a portion of the second regions is closer to an opening around a body or an opening around a leg of the disposable wearable article than the first regions.

4 Claims, 6 Drawing Sheets

(51) Int. Cl.
| | |
|---|---|
| *A61F 13/15* | (2006.01) |
| *A61F 13/49* | (2006.01) |
| *B29C 48/305* | (2019.01) |
| *B32B 3/00* | (2006.01) |
| *B32B 3/04* | (2006.01) |
| *B32B 3/08* | (2006.01) |
| *B32B 27/00* | (2006.01) |
| *B32B 27/06* | (2006.01) |
| *B32B 41/00* | (2006.01) |

(52) U.S. Cl.
CPC ............... *B32B 3/04* (2013.01); *B32B 3/08* (2013.01); *B32B 27/06* (2013.01)

(58) Field of Classification Search
CPC ............ A61F 13/156; A61F 13/1568; A61F 13/15682; A61F 13/40; A61F 13/49; B32B 3/00; B32B 3/04; B32B 3/08; B32B 27/00; B32B 27/06
USPC ................ 156/60, 64, 350, 351, 378, 379
See application file for complete search history.

(56) References Cited

U.S. PATENT DOCUMENTS

| | | | |
|---|---|---|---|
| 2012/0022490 | A1 | 1/2012 | Marche et al. |
| 2014/0073211 | A1* | 3/2014 | Bruce ................. B32B 5/08 |
| | | | 156/244.19 |
| 2018/0140473 | A1* | 5/2018 | Koshijima ........ A61F 13/15804 |

FOREIGN PATENT DOCUMENTS

| | | |
|---|---|---|
| EP | 2135590 A1 | 12/2009 |
| JP | 3054930 B2 | 6/2000 |
| JP | 2008-106378 A | 5/2008 |
| JP | 2008106378 * | 5/2008 |
| JP | 2010-503781 A | 2/2010 |
| JP | 2012-235806 A | 12/2012 |
| JP | 2015-529165 A | 10/2015 |
| JP | 2016-073827 A | 5/2016 |
| WO | 2015/025760 A1 | 2/2015 |
| WO | 2015/056711 A1 | 4/2015 |
| WO | 2015/056771 A1 | 4/2015 |

OTHER PUBLICATIONS

Europe Patent Office, "Search Report for European Patent Application No. 18904905.9," Oct. 15, 2021.

* cited by examiner

Fig. 7(a)
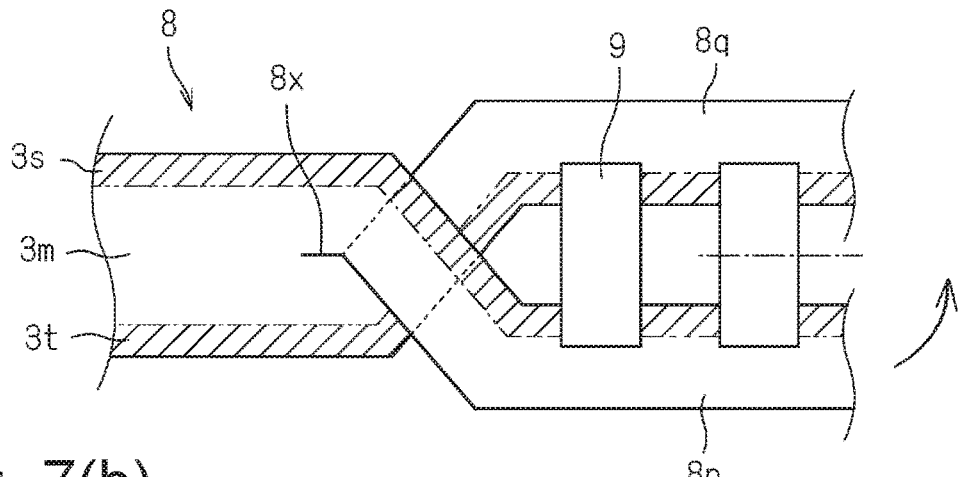
Fig. 7(b)
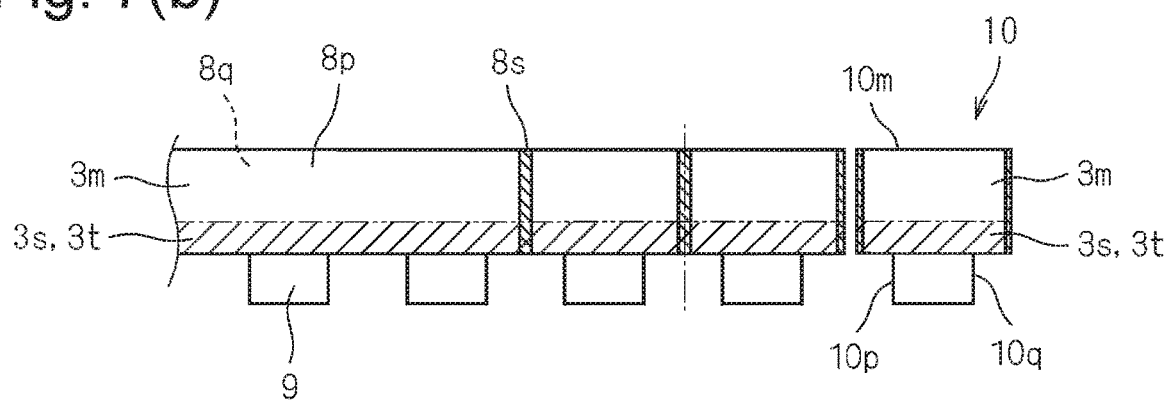
Fig. 8(a)
Fig. 8(b)
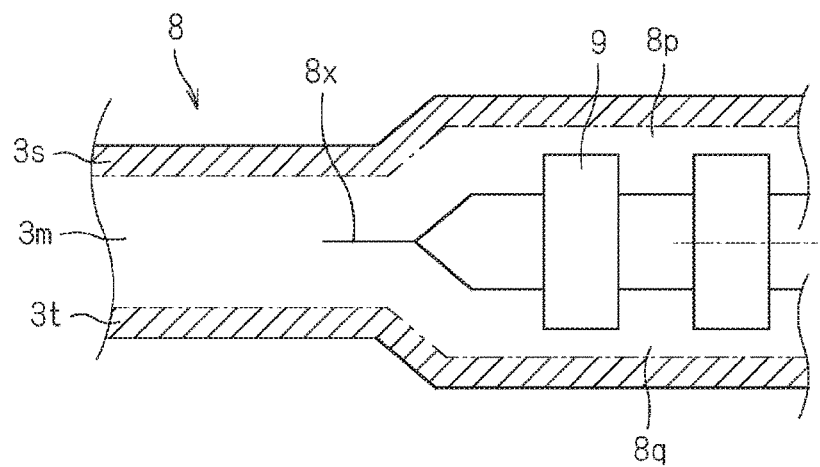

Fig. 10 --Prior Art--

STRETCHABLE SHEET MANUFACTURING METHOD

RELATED APPLICATIONS

The present application is National Phase of International Application No. PCT/JP2018/046144 filed Dec. 14, 2018, and claims a priority from Japanese Application No. 2018-019662, filed Feb. 6, 2018, the disclosure of which is hereby incorporated by reference herein in its entirety.

TECHNICAL FIELD

The present invention relates to a stretchable sheet manufacturing method.

BACKGROUND ART

A stretchable sheet that is excellent in stretchability is used for the back sheet of a disposable diaper and the like. FIG. 10 is a schematic illustration showing a method for manufacturing the stretchable sheet. As shown in FIG. 10, a thermoplastic elastic resin is extruded from a T die 111 to form a film-shape object 103' in a molten state. Then, the film-shape object 103' is cooled by a chill roller 120. Then, the cooled film-shape object 103" is sandwiched between two sheets of continuous nonwoven fabric 102 and at the same time, embossing is performed thereon. The embossing is performed by pressurization and nipping with an embossing roller 112 having a multiplicity of dot-shape convex portions 112*a* formed on the surface thereof and a backup roller 113. A stretchable sheet 101 in which the layers are joined and integrated by the embossing is wounded by a winding roller 116. As the nonwoven fabric 102, a nonwoven fabric is used that is stretchable at least in a lateral direction (a direction vertical to the flow direction and the thickness direction of the nonwoven fabric 102) (for example, see Patent Literature 1).

PRIOR ART LITERATURE

Patent Literature

[Patent Literature 1] Japanese Patent No. 3054930

SUMMARY OF THE INVENTION

Problem to be Solved by the Invention

For example, if a stretchable sheet in which the stretching characteristics vary along the width direction thereof is used, a high contraction stress can be provided to the parts of a disposable diaper around the waist and around the legs.

However, the stretchable sheet manufactured by the method shown in FIGS. 5(*a*) and 5(*b*) are uniforms in stretching characteristics because the thickness of the film-shape object 103" is uniform.

In view of such circumstances, a problem to be solved by the present invention is to provide a stretchable sheet in which the stretching characteristics vary along the width direction, a disposable wearing article using the stretchable sheet in which the stretching characteristics vary along the width direction, and a method for manufacturing the same.

Means for Solving the Problem

To solve the above-mentioned problem, the present invention provides a stretchable sheet structured as follows:

The stretchable sheet is provided with: (a) a sheet body in which an elastic resin material having a main component of a thermoplastic elastic resin is molded into a sheet shape; and (b) a base sheet laminated and joined to at least one of an opposing pair of main surfaces of the sheet body. The sheet body includes at least two first and second regions adjoining each other in a width direction and each extending in a direction vertical to the width direction. The thickness of the second region is greater than the thickness of the first region. The base sheet is laminated and joined to the first and second regions of the sheet body.

According to the above-described structure, the first and second regions adjoining in the width direction of the sheet body vary in stretching characteristics according to the variations in thickness. For this reason, the stretchable sheet in which the base sheet is laminated and joined to the first and second regions of the sheet body varies in stretching characteristics along the width direction.

Preferably, the sheet body includes: (i) the first region in a center of the sheet body in the width direction; and (ii) the second region on each side of the sheet body in the width direction.

In this case, in the sheet body, the thickness of the second region on each side in the width direction is greater than the thickness of the first region in the center in the width direction.

Moreover, the present invention provides a disposable wearing article structured as follows:

The disposable wearing article is structured so that an opening around a body and a pair of openings around legs are formed, and includes the above-described stretchable sheet. The stretchable sheet is disposed so that at least a portion of the second region is closer to the opening around the body or the openings around the legs than the first region.

In this case, a high contraction stress can be provided to at least one of the part around waist and the parts around the legs of the disposable wearing article.

Moreover, to solve the above-mentioned problem, the present invention provides a stretchable sheet manufacturing method structured as follows:

In the stretchable sheet manufacturing method, (i) an elastic resin material having a main component of a thermoplastic elastic resin which elastic resin material is heat-melted is extruded into a sheet shape on a die and made to have a thickness that varies along a width direction, and is then cooled to a temperature range in which the elastic resin material elastically deforms, to form a sheet body that varies in thickness along the width direction, and (ii) a base sheet is laminated and joined to at least one of an opposing pair of main surfaces of the sheet body.

According to the above-described method, since the sheet body has a thickness that varies along the width direction, the stretching characteristics thereof vary according to the variations in thickness. For this reason, the stretchable sheet in which the base sheet is laminated and joined to at least one of the main surfaces of the sheet body varies in stretching characteristics along the width direction.

Specifically, in various modes as described below, a sheet body that varies in thickness along the width direction can be formed by extruding the heat-melted elastic resin material into a sheet shape on the die to make the thickness thereof vary along the width direction.

In a first mode, an intermediate product of the elastic resin material extruded in a sheet shape on the die is stretched in the uniaxial direction to thereby contract the width of the intermediate product to make the thickness of the intermediate product vary along the width direction, and is then cooled to the temperature range to form the sheet body that varies in thickness along the width direction.

For example, when the intermediate product is stretched to contract the width of the intermediate product, the thickness is made to vary along the width direction by using a phenomenon in which the thicknesses of the end parts of the intermediate product in the width direction are greater than the thickness of the middle part thereof in the width direction between the end parts in the width direction. The thickness may be made to vary along the width direction by forcibly deforming the intermediate product by blowing hot air to the intermediate product or pressing a tool against the intermediate product when the intermediate product is stretched to thereby contract the width of the intermediate product.

In a second mode, the heat-melted elastic resin material is discharged from the lip of the die having parts that are different in lip width, to form an intermediate product that is made to vary in thickness along the width direction, and the intermediate product is cooled to the temperature range to form the sheet body that varies in thickness along the width direction.

In this case, the thickness is made to vary along the width direction according to the lip width of the discharge outlet.

In a third mode, at least one of one end side in the width direction and the other end side in the width direction of the elastic resin material extruded in a sheet shape from the die is folded back toward the center in the width direction and overlaid to form an intermediate product that is made to vary in thickness along the width direction, and the intermediate product is cooled to the temperature range to form the sheet body that varies in thickness along the width direction.

In this case, the thickness is made to vary along the width direction according to the presence or absence of the overlap by folding back.

In a fourth mode, on a predetermined position in the width direction of an intermediate product of the elastic resin material extruded into a sheet shape from the die, a sheet-shape addition different from the intermediate product is laminated to form a laminated body that is made to vary in thickness along the width direction, and the laminated body is cooled to the temperature range to form the sheet body that varies in thickness along the width direction.

In this case, the thickness is made to vary along the width direction according to the presence or absence of the lamination of the addition.

Moreover, to solve the above-mentioned problem, the present invention provides a disposable wearing article manufacturing method structured as follows:

The disposable wearing article manufacturing method is provided with: (i) a first step in which an elastic resin material having a main component of a thermoplastic elastic resin which elastic resin material is heat-melted is extruded into a sheet shape on a die and made to have a thickness that varies along a width direction, to form a sheet body including a first region in a center in the width direction and a second region on each side in the width direction, adjoining the first region and being greater in thickness than the first region; then, a base sheet is laminated and joined to at least one of an opposing pair of main surfaces of the sheet body to form a stretchable sheet; (ii) a second step in which a slit extending in a direction vertical to the width direction of the stretchable sheet and passing through the first region of the sheet body is formed in the stretchable sheet, and the stretchable sheet is divided into a first divisional sheet and a second divisional sheet; (iii) a third step in which a space between the first divisional sheet and the second divisional sheet is widened; (iv) a fourth step in which crotch portions are disposed at intervals in a length direction of the first and second divisional sheets so as to lie astride the first divisional sheet and the second divisional sheet the space between which is widened, and are joined to the first divisional sheet and the second divisional sheet; (v) a fifth step in which the first divisional sheet and the second divisional sheet are superposed on each other by folding at the crotch portions, and the first divisional sheet and the second divisional sheet are joined together between the adjoining crotch portions to form side seal portions; and (vi) a sixth step in which the first divisional sheet and the second divisional sheet are cut at the side seal portions so as to be divided into pieces.

By the above-described method, the front body portion and the rear body portion of the disposable wearing article are formed by the first and second divisional sheets into which the stretchable sheet is divided. By disposing the second region being greater in thickness than the first region in the part around the waist or the parts around the legs of the disposable wearing article, a high contraction stress can be provided to the part around the waist or the parts around the legs.

Moreover, to solve the above-mentioned problem, the present invention provides a disposable wearing article manufacturing method structured as follows:

The disposable wearing article manufacturing method is provided with: (i) a first step in which a first elastic resin material having a main component of a first thermoplastic elastic resin which first elastic resin material is heat-melted is extruded into a sheet shape on a first die and made to have a thickness that varies along a width direction, to form a first sheet body including a first region in a center in the width direction and a second region on each side in the width direction, adjoining the first region and being greater in thickness than the first region; then, a first base sheet is laminated and joined to at least one of an opposing pair of main surfaces of the first sheet body to form a first stretchable sheet; (ii) a second step in which a second elastic resin material having a main component of a second thermoplastic elastic resin which second elastic resin material is heat-melted is extruded into a sheet shape on a second die and made to have a thickness that varies along a width direction, to form a second sheet body including a third region in a center in the width direction and a fourth region on each side in the width direction, adjoining the third region and being greater in thickness than the third region; then, a second base sheet is laminated and joined to at least one of an opposing pair of main surfaces of the second sheet body to form a second stretchable sheet; (iii) a third step in which the first stretchable sheet and the second stretchable sheet are placed with a predetermined space therebetween; (iv) a fourth step in which crotch portions are disposed at intervals in a length direction of the first stretchable sheet and the second stretchable sheet so as to lie astride the first stretchable sheet and the second stretchable sheet placed with the predetermined space therebetween, and are joined to the first stretchable sheet and the second stretchable sheet; (v) a fifth step in which the first stretchable sheet and the second stretchable sheet are superposed on each other by folding at the crotch portions, and the first stretchable sheet and the second stretchable sheet are joined together between the adjoining crotch portions to form side seal portions; and (vi) a sixth step in which the first stretchable sheet and the second stretchable sheet are cut at the side seal portions so as to be divided into pieces.

By the above-described method, the front body portion and the rear body portion of the disposable wearing article are formed by the first and second stretchable sheets. By disposing the second region being greater in thickness than the first region and the fourth region being greater in thickness than the third region in the part around the waist and the parts around the legs of the disposable wearing article, a high contraction stress can be provided to the part around the waist and the parts around the legs of the disposable wearing article.

Effects of the Invention

According to the present invention, a stretchable sheet in which the stretching characteristics vary along the width direction, a disposable wearing article using the stretchable sheet in which the stretching characteristics vary along the width direction, and a method for manufacturing the same can be provided.

BRIEF DESCRIPTION OF THE DRAWINGS

FIGS. 7(a) and 7(b) are explanations of the manufacturing process for manufacturing the disposable wearing article (second embodiment).

FIGS. 8(a) and 8(b) are explanatory views of the disposable wearing article manufacturing process (second embodiment).

FIG. 10 is a schematic illustration showing the method for manufacturing the stretchable sheet (first conventional example).

MODE FOR CARRYING OUT THE INVENTION

Hereinafter, embodiments of the present invention will be described with reference to the drawings.

<First Embodiment> A first embodiment will be described with reference to FIGS. 1 to 5.

Figure 1:
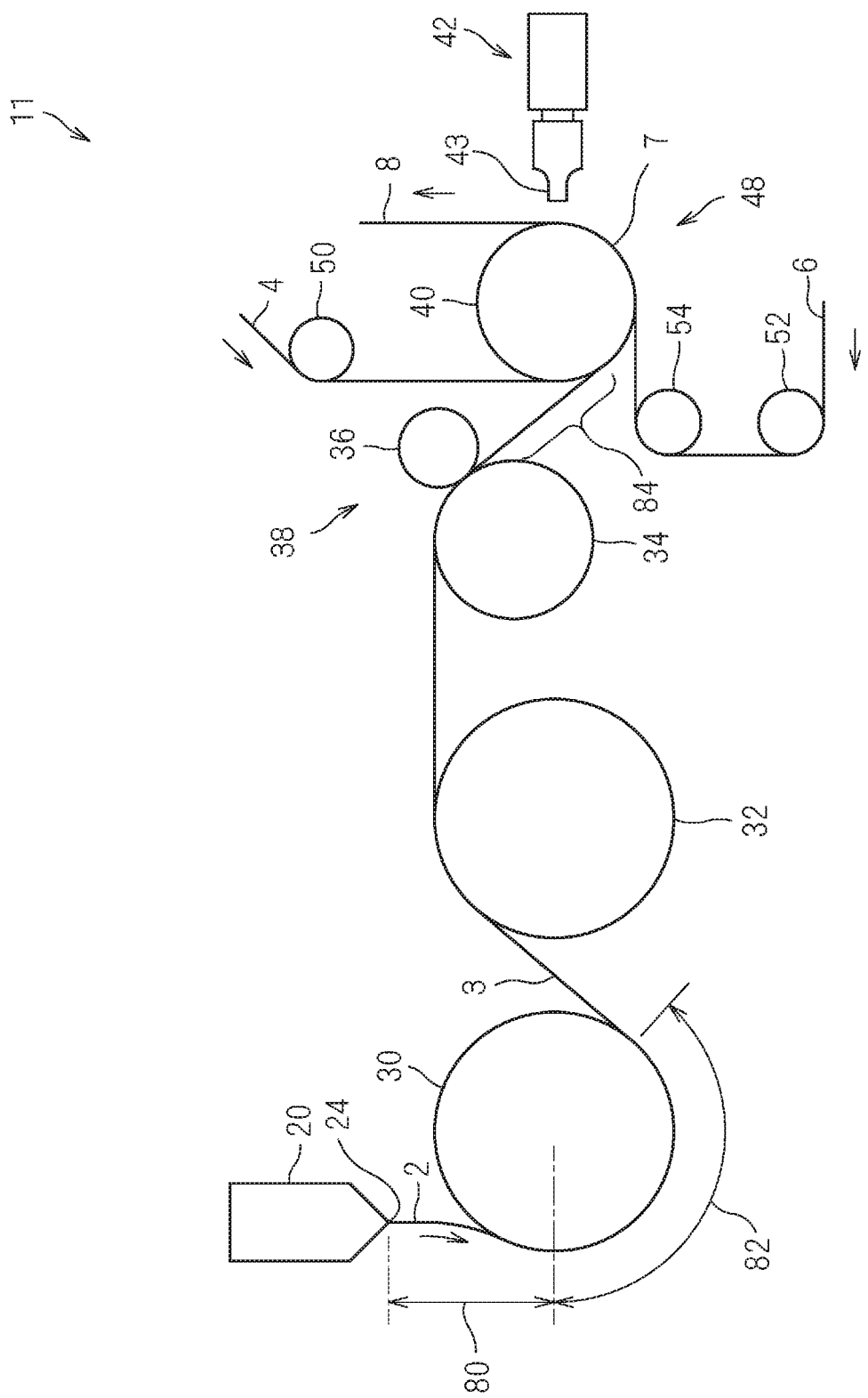
FIG. 1 is a schematic illustration showing the general structure of a stretchable sheet manufacturing apparatus (first embodiment).

FIG. 1 is a schematic illustration showing the general structure of a stretchable composite sheet manufacturing apparatus 11. As shown in FIG. 1, the stretchable composite sheet manufacturing apparatus 11 is provided with a die 20, a cooling roller 30, a stretching mechanism 38, a laminating mechanism 48, and a non-illustrated control device. The control device controls the die 20, the cooling roller 30, the stretching mechanism 38 and the laminating mechanism 48 so as to operate in cooperation with one another.

The die 20 forms a sheet-shape intermediate product 2 by discharging a heat-melted elastic resin material into a sheet shape from a lip 24. The elastic resin material has a main component of a thermoplastic elastic resin, and is heat-melted to a temperature higher than the temperature range in which the elastic resin material elastically deforms.

The cooling roller 30 is disposed below the die 20. The intermediate product 2 discharged from the lip 24 of the die 20 is stretched in a first section 80 to when it reaches the cooling roller 30. That is, the cooling roller 30 rotates at a circumferential speed higher than the feeding speed of the elastic resin material when it is discharged from the discharge outlet of the die 20, and contracts the width (the dimension in the direction vertical to the plane of the figure in FIG. 1) of the intermediate product 2 by stretching the intermediate product 2 in the uniaxial direction until the thickness of the intermediate product 2 becomes a predetermined value.

At this time, the thickness is made to vary along the width direction by using a phenomenon in which the thicknesses of both end parts of the intermediate product 2 in the width direction are greater than the thickness of the middle part thereof in the width direction between the end parts in the width direction. That is, generally, when a sheet is manufactured by discharging a heat-melted resin material into a sheet shape and stretching it, only the middle part in the width direction that is uniform in thickness is used, and both end parts in the width direction that are different in thickness are removed. On the contrary, since the thickness of the elastic resin material extruded into a sheet shape on a die is made to vary along the width direction, both end parts of the intermediate product 2 in the width direction are also used positively.

In another mode described later, the thickness of the elastic resin material extruded in a sheet shape on the die 20 may be made to vary along the width direction.

In the cooling roller 30, a non-illustrated flow path where a coolant flows is formed, and in a second section 82 in which the intermediate product 2 is in contact with the outer peripheral surface of the cooling roller 30, the cooling roller 30 cools the intermediate product 2 to the temperature range in which the elastic resin material forming the intermediate product 2 elastically deforms, and solidifies it. Thereby, the intermediate product 2 that is made to vary in thickness along the width direction becomes a sheet-shape sheet body 3 that varies in thickness along the width direction in the second section 82, and is drawn from the cooling roller 30.

The sheet body 3 is sent to the stretching mechanism 38 by way of a guide roller 32. The guide roller 32 may be provided with a cooling function.

The stretching mechanism 38 includes a drawing roller 34, a pinch roller 36 and a stretching roller 40. The sheet body 3 is sandwiched between the drawing roller 34 and the pinch roller 36 so as not to slide along the outer peripheral surface of the drawing roller 34. The rotation of the drawing roller 34 synchronizes with the rotation of the cooling roller 30.

The sheet body 3 is stretched in a third section 84 from when it is between the drawing roller 34 and the pinch roller 36 to when it reaches the stretching roller 40. That is, the stretching roller 40 rotates at a circumferential speed higher than that of the drawing roller 34 to stretch the sheet body 3 at a predetermined magnification. The sheet body 3 being stretched is along the outer peripheral surface of the stretching roller 40.

The laminating mechanism 48 supplies continuous first nonwoven fabric 4 as a first base sheet to the stretching roller 40 through a guide roller 50, and supplies continuous second nonwoven fabric 6 as a second base sheet to the stretching roller 40 through guide rollers 52 and 54. The sheet body 3 stretched along the stretching roller 40 is sandwiched between the first nonwoven fabric 4 and the second nonwoven fabric 6, so that a laminated body 7 in which the sheet body 3 and the first and second nonwoven fabrics 4 and 6 are laminated is formed.

The laminated body 7 moves with the rotation of the stretching roller 40, and passes between the stretching roller 40 and a horn 43 of an ultrasonic joining apparatus 42. The horn 43 comes into contact with and separates from the stretching roller 40 and when the laminated body 7 is sandwiched between the stretching roller 40 and the horn 43, the sheet body 3 and the first and second nonwoven fabrics 4 and 6 are supersonically joined. Thereby, a stretchable sheet 8 in which the sheet body 3 and the first and second nonwoven fabrics 4 and 6 are intermittently joined is formed and drawn from the laminating mechanism 48. Regarding the first and second nonwoven fabrics 4 and 6, parts thereof directly opposing without the sheet body 3 in between may be supersonically joined together.

Specifically, the stretching roller 40 has, on its outer peripheral surface, a plurality of non-illustrated protrusions formed at intervals from one another, and functions as an anvil. Of the laminated body 7, the parts sandwiched between the protrusions of the stretching roller 40 and the horn 43 is supersonically joined. By the supersonic joining, desired parts can be easily and accurately joined.

Instead of supersonic joining, the sheet body 3 and the first and second nonwoven fabrics 4 and 6 of the laminated body 7 may be heat-welded by heat sealing or the like, or the sheet body 3 and the first and second nonwoven fabrics 4 and 6 of the laminated body 7 may be bonded by using an adhesive agent. Two or more joining modes may be combined.

The stretching roller 40 serves as both the stretching mechanism 38 and the laminating mechanism 48. While this simplifies the structure of the stretchable composite sheet manufacturing apparatus 11, a structure provided with separate rollers as the stretching mechanism 38 and the laminating mechanism 48 may be adopted.

Figure 2:
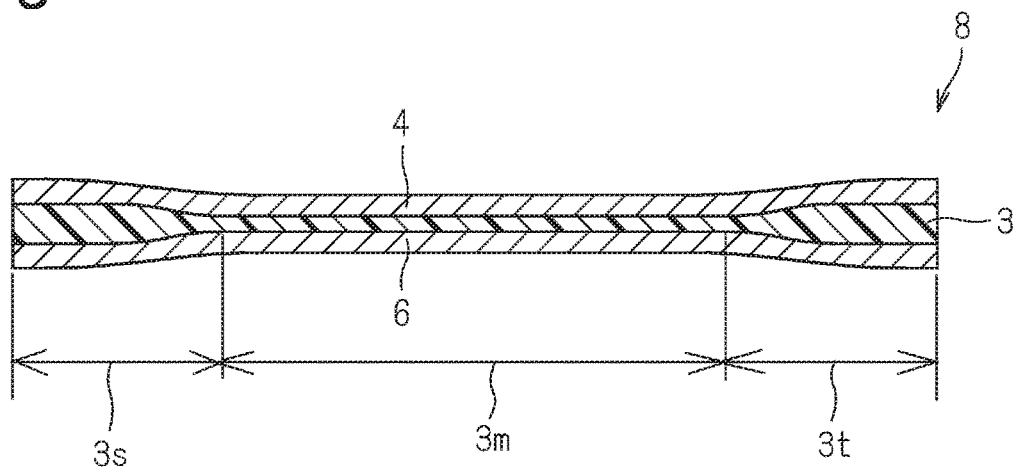
FIG. 2 is a cross-sectional view of a stretchable sheet (first embodiment).

FIG. 2 is a cross-sectional view of the stretchable sheet 8 which is cut in the width direction. As shown in FIG. 2, the stretchable sheet 8 is provided with: the sheet body 3 in which an elastic resin material having a main component of a thermoplastic elastic resin is formed into a sheet shape; and the first and second nonwoven fabrics 4 and 6 as the base sheets laminated and joined to an opposing pair of main surfaces of the sheet body 3, respectively. The sheet body 3 includes two first and second regions 3m, and 3s and 3t adjoining each other in the width direction and each extending in a direction vertical to the width direction, that is, the first region 3m in the center of the sheet body 3 in the width direction and the second regions 3s and 3t on both sides of the sheet body 3 in the width direction. The thicknesses of the second regions 3s and 3t are greater than the thickness of the first region 3m. The first and second nonwoven fabrics 4 and 6 are laminated and joined to the first and second regions 3m, and 3s and 3t of the sheet body 3.

The first and second regions 3m, and 3s and 3t adjoining in the width direction of the sheet body 3 vary in stretching characteristics according to the variations in thickness. For this reason, the stretchable sheet 8 in which the first and second nonwoven fabrics 4 and 6 are laminated and joined to the first and second regions 3m, and 3s and 3t of the sheet body 3 varies in stretching characteristics along the width direction.

The laminating mechanism 48 may supply only one of the first and second nonwoven fabrics 4 and 6 to the stretching roller 40 so that a laminated body in which the sheet body 3 and only one of the first and second nonwoven fabrics 4 and 6 are laminated is formed. The stretchable sheet manufactured in this case is provided with a base sheet (the first nonwoven fabric 4 or the second nonwoven fabric 6) laminated and joined to one of the opposing pair of main surfaces of the sheet body 3.

Moreover, the stretching mechanism 38 may be omitted. In this case, a stretchable sheet can be manufactured in which the sheet body 3 is laminated and joined to the first and/or the second nonwoven fabric 4 and/or 6 without being stretched.

It is desirable that the thermoplastic elastic resin as the material of the sheet body 3 be a thermoplastic resin that exhibits rubber elasticity at room temperature; for example, an appropriate kind may be selected from among thermoplastic elastomers defined and classified in JIS K 6418:2007 (ISO 18064:2003). For example, a thermoplastic elastomer that elastically deforms in a temperature range of not more than approximately 100 degrees C. is used.

Specific examples include an olefinic elastomer such as "VERSIFY" (trademark) of The Dow Chemical Company, a propylene elastomer such as "Vistamaxx" (trademark) of Exxon Mobil Corporation, and a styrene elastomer such as "Quintac" (trademark) of Zeon Corporation.

Next, referring to FIG. 1, the method for manufacturing the stretchable sheet 8 will be described.

First, an elastic resin material having a main component of a thermoplastic elastic resin which elastic resin material is heat-melted is extruded into a sheet shape on the die 20 and made to have a thickness that varies along the width direction, and is then cooled to a temperature range in which the elastic resin material elastically deforms, to form the sheet body 3 that varies in thickness along the width direction. Then, the base sheets (the first and second nonwoven fabrics 4 and 6) are laminated and joined to at least one of the opposing pair of main surfaces of the sheet body 3.

According to the above-described method, since the sheet body 3 has a thickness that varies along the width direction, the stretching characteristics thereof vary according to the variations in thickness. For this reason, the stretchable sheet in which the base sheets are laminated and joined to at least one of the main surfaces of the sheet body varies in stretching characteristics along the width direction.

Specifically, in various modes as described below, a sheet body that varies in thickness along the width direction can be formed by extruding the heat-melted elastic resin material into a sheet shape on the die 20 to make the thickness thereof vary along the width direction.

Figure 3A:
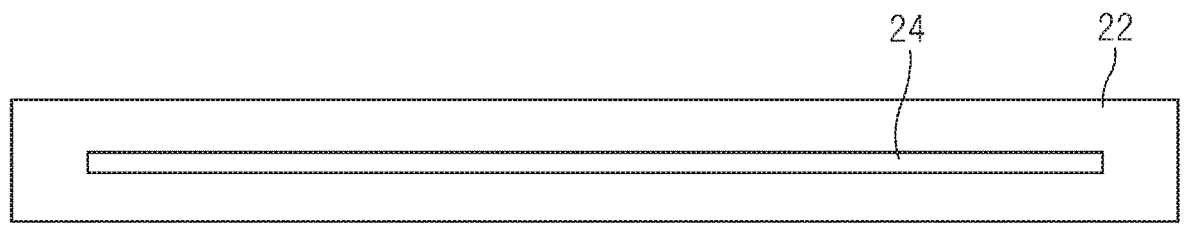
FIGS. 3(a) and 3(b) are bottom views of a die (first embodiment).

A first mode will be described. FIG. 3(a) is a bottom view of the die 20 used in the first mode. As shown in FIG. 3(a), the lip 24 as the discharge outlet for the heat-melted elastic resin material is formed on a bottom surface 22 of the die 20. The lip 24 has a uniform lip width. The intermediate product 2 of the elastic resin material extruded on the die 20 and discharged from the lip 24 is stretched in the uniaxial direction to thereby contract the width of the intermediate product 2 to make the thickness of the intermediate product 2 vary along the width direction, and is then cooled to a temperature range in which the elastic resin material elastically deforms, to form the sheet body 3 that varies in thickness along the width direction.

For example, when the intermediate product 2 is stretched in the uniaxial direction to contract the width of the intermediate product 2, the thickness is made to vary along the width direction by using a phenomenon in which the thicknesses of the end parts of the intermediate product 2 in the width direction are greater than the thickness of the middle part thereof in the width direction. Alternatively, the thickness may be made to vary along the width direction by forcibly deforming the intermediate product 2 by blowing hot air to the intermediate product 2 or pressing a tool against the intermediate product 2 when the intermediate product 2 is stretched in the uniaxial direction to contract the width of the intermediate product 2.

Figure 3B:
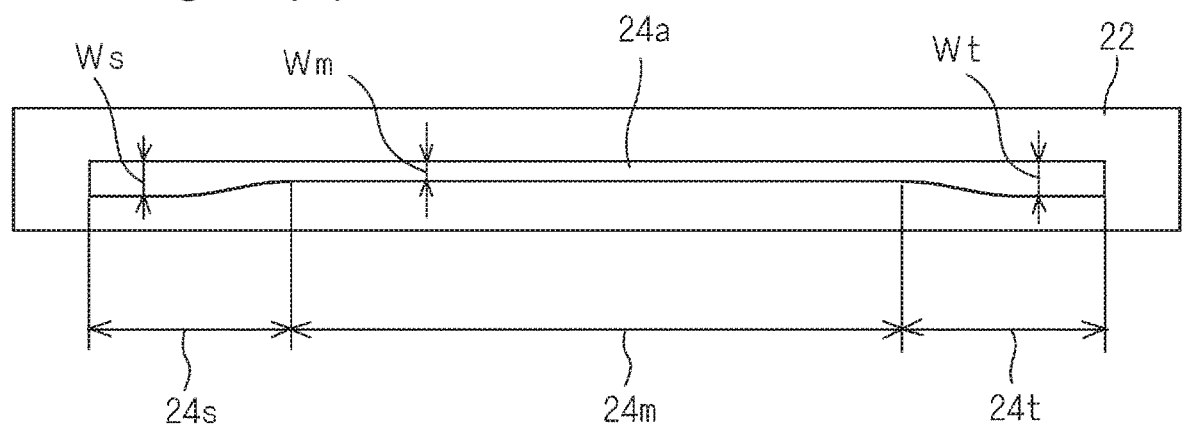

A second mode will be described. FIG. 3(b) is a bottom view of the die 20 used in the second mode. As shown in FIG. 3(b), a lip 24a formed on the bottom surface 22 of the die 20 has parts 24m, 24s and 24t that are different in lip width. That is, the lip widths Ws and Wt of the end parts 24s and 24t are greater than the lip width Wm of the middle part 24m between the end parts 24s and 24t.

When the heat-melted elastic resin material is discharged from the lip 24a having the parts 24m, 24s and 24t that are different in lip width, an intermediate product that is made to vary in thickness along the width direction according to the lip width can be formed. This intermediate product is cooled to a temperature range in which the elastic resin material elastically deforms, to form a sheet body that varies in thickness along the width direction.

Figure 4A:
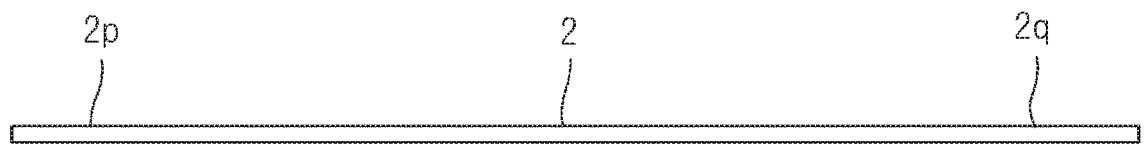
FIGS. 4(a) and 4(b) are explanatory views of sheet body formation (first embodiment.
Figure 4B:
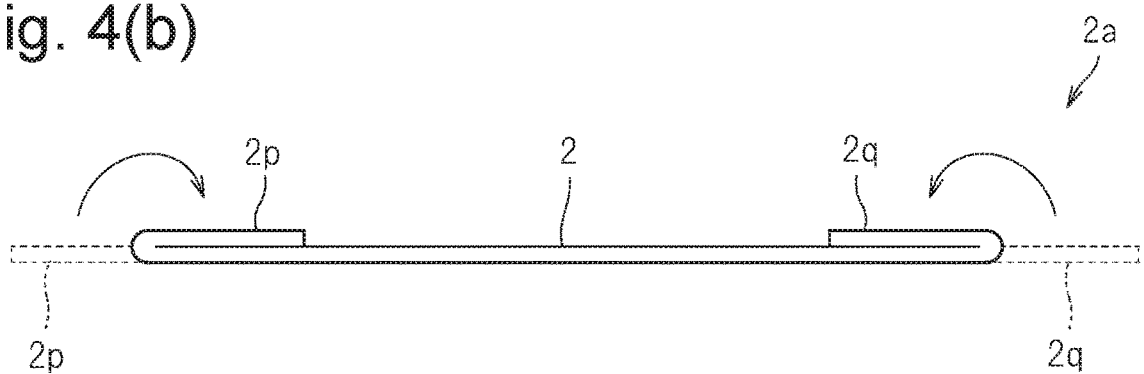

A third mode will be described. FIGS. 4(a) and 4(b) are explanatory views of sheet body formation, and shows a cross section of the elastic resin material extruded into a sheet shape from the die which elastic resin material is cut in the width direction. As shown in FIG. 4(a), the elastic resin material extruded into a sheet shape from the die is sheet-shape. This is folded back as shown in FIG. 4(b). That is, one end side 2p in the width direction of the elastic resin material extruded into a sheet shape from the die is folded back toward the center in the width direction and overlaid, and the other end side 2q in the width direction is also folded back toward the center in the width direction and overlaid to form an intermediate product 2a that is made to vary in thickness along the width direction according to the presence or absence of the overlap by the folding back. By cooling this intermediate product 2a to a temperature range in which the elastic resin material elastically deforms, a sheet body that varies in thickness along the width direction is formed. It may be only either one of the one end side 2p in the width direction of the elastic resin material and the other end side 2q in the width direction that is folded back toward the center in the width direction and overlaid.

Figure 5A:
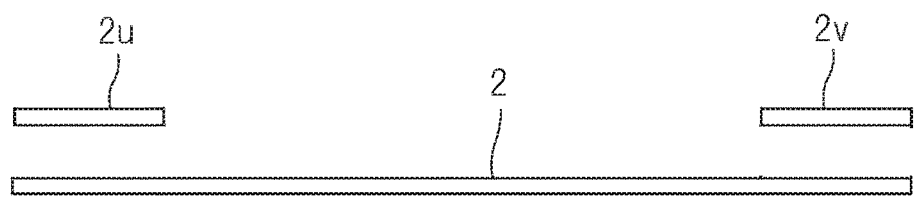
FIGS. 5(a) and 5(b) are explanatory views of sheet body formation (first embodiment).
Figure 5B:
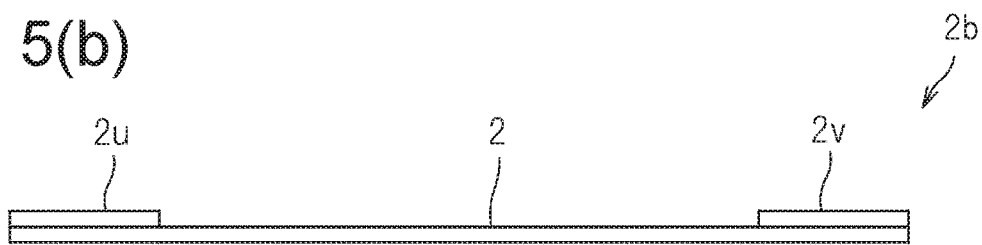

A forth mode will be described. FIGS. 5(a) and 5(b) are explanatory views of sheet body formation, and shows a cross section of the intermediate product 2 and additions 2u and 2v which are cut in the width direction. As shown in FIG. 5(a), sheet-shape additions 2u and 2v different from the intermediate product 2 of the elastic resin material extruded from the die are prepared. The additions 2u and 2v may be either sheet-shape extrusions from the die like the intermediate product 2 or previously manufactured ones (for example, ones drawn out from a roller).

As shown in FIG. 5(b), the sheet-shape additions 2u and 2v different from the intermediate product 2 are laminated on predetermined positions in the width direction of the intermediate product 2 of the elastic resin material extruded into a sheet shape from the die, to form a laminated body 2b that is made to vary in thickness along the width direction according to the presence or absence of the lamination of the additions 2u and 2v. By cooling this laminated body 2b to a temperature range in which the elastic resin material of the intermediate product 2 elastically deforms, a sheet body that varies in thickness along the width direction is formed.

When the additions 2u and 2v are extrusions obtained by extruding an elastic resin material into a sheet shape by a die like the intermediate product 2, the laminated body 2b is cooled to a temperature range in which the elastic resin material of the intermediate product 2 and the additions 2u and 2v elastically deforms, to form a sheet body that varies in thickness along the width direction.

Figure 6:
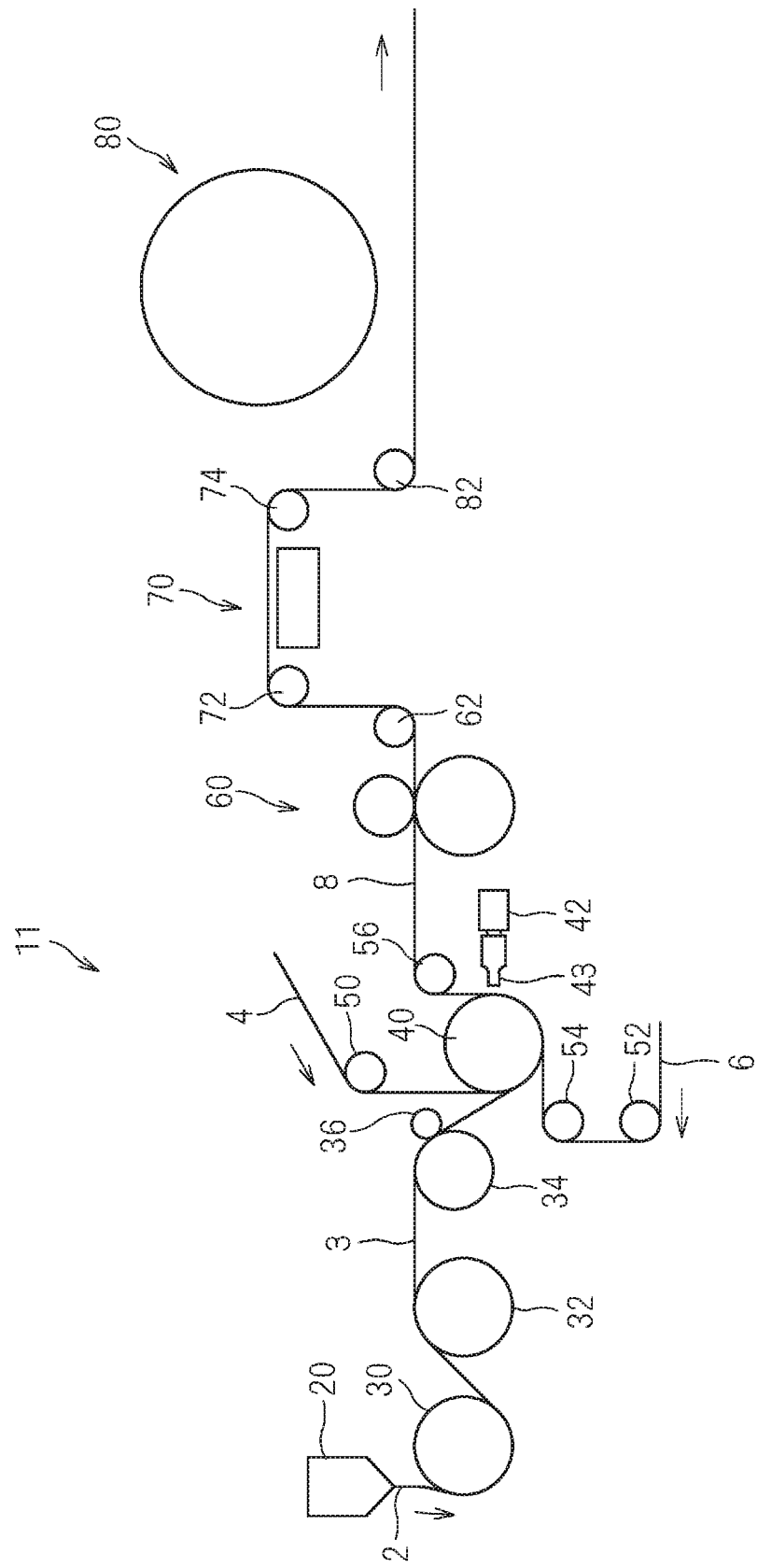
FIG. 6 is an explanation of a manufacturing process for manufacturing a disposable wearing article (second embodiment).

<Second Embodiment> A second embodiment will be described with reference to FIGS. 6 to 8. FIGS. 6 to 8 are explanatory views of the process for manufacturing a disposable wearing article.

First, the process for manufacturing a disposable wearing article will be described. As shown in FIG. 6, the stretchable sheet 8 manufactured by the stretchable composite sheet manufacturing apparatus 11 of the first embodiment is conveyed through guide rollers 56, 62, 72, 74 and 82, and after passing through a slitter 60, a widening mechanism 70 and an absorber pasting mechanism 80, the stretchable sheet 8 is divided into pieces by a non-illustrated cutting mechanism.

Specifically, as shown in FIGS. 7(a) and 8(a), the stretchable sheet 8 is formed as in the first embodiment. That is, an elastic resin material having a main component of a thermoplastic elastic resin which elastic resin material is heat-melted is extruded into a sheet shape on the die 20 and made to have a thickness that varies along the width direction, to form the sheet body 3 including the first region 3m in the center in the width direction and the second regions 3s and 3t on both sides in the width direction, adjoining the first region 3m and being greater in thickness than the first region 3m; then, at least one of the first and second nonwoven fabrics 4 and 6 as the base sheets is laminated and joined to at least one of the opposing pair of main surfaces of the sheet body 3 to form the stretchable sheet 8 (first step).

Then, at the slitter 60, as shown in FIGS. 7(a) and 8(a), a slit 8x extending in a direction vertical to the width direction of the stretchable sheet 8 is formed in the stretchable sheet 8, and the stretchable sheet 8 is divided into a first divisional sheet 8p and a second divisional sheet 8q. The slit 8x passes through the first region 3m of the sheet body (second step).

Then, at the widening mechanism 70, as shown in FIG. 7(a), the first divisional sheet 8p and the second divisional sheet 8q are crossed to widen the space between the first divisional sheet 8p and the second divisional sheet 8q. The space between the first divisional sheet 8p and the second divisional sheet 8q may be widened without the first divisional sheet 8p and the second divisional sheet 8q being crossed as shown in FIG. 8(a) (third step).

Then, at the absorber pasting mechanism 80, as shown in FIGS. 7(a) and 8(a), crotch portions 9 each including an absorber are disposed at intervals in the length direction of the first divisional sheet 8p and the second divisional sheet 8q (the horizontal direction in FIGS. 7(a) and 8(a)) so as to lie astride the first divisional sheet 8p and the second divisional sheet 8q the space between which is widened, and are joined to the first divisional sheet 8p and the second divisional sheet 8q. The absorber may be added to the crotch portions 9 after the crotch portions 9 are joined to the first and second divisional sheets 8p and 8q (fourth step).

Then, as shown in FIG. 7(b), the first divisional sheet 8p and the second divisional sheet 8q are superposed on each other by folding at the crotch portions 9, and the first divisional sheet 8p and the second divisional sheet 8q are joined together by heat sealing or the like between the adjoining crotch portions 9 to form side seal portions 8s (fifth step).

Then, the first divisional sheet 8*p* and the second divisional sheet 8*q* are cut at the side seal portions 8*s* so as to be divided into ten pieces (sixth step).

In each divisional piece 10, the first divisional sheet 8*p* and the second divisional sheet 8*q* are joined together by a pair of side seal portions 8*s* that are cut. The divisional piece 10 is a disposable wearing article 10 structured so that an opening 10*m* around the body is formed by the first divisional sheet 8*p* and the second divisional sheet 8*q* and a pair of openings 10*p* and 10*q* around the legs are formed by the first divisional sheet 8*p*, the second divisional sheet 8*q* and the crotch portion 9. The front body portion and the rear body portion of the disposable wearing article 10 are formed by the first and second divisional sheets 8*p* and 8*q* into which the stretchable sheet 8 is divided.

When the first divisional sheet 8*p* and the second divisional sheet 8*q* are crossed to widen the space between the first divisional sheet 8*p* and the second divisional sheet 8*q* as shown in FIG. 7(*a*), as shown in FIG. 7(*b*), in the disposable wearing article 10, the stretchable sheet 8 is disposed so that the hatched second regions 3*s* and 3*t* are closer to the openings 10*p* and 10*q* around the legs than the first region 3*m*. The thicknesses of the second regions 3*s* and 3*t* are greater than the thickness of the first region 3*m*. For this reason, a high contraction stress can be provided to the parts around the legs of the disposable wearing article 10.

When the space is widened without the first divisional sheet 8*p* and the second divisional sheet 8*q* being crossed as shown in FIG. 8(*a*), as shown in FIG. 8(*b*), in a disposable wearing article 10*a*, the stretchable sheet 8 is disposed so that the hatched second regions 3*s* and 3*t* are closer to the opening 10*m* around the body than the first region 3*m*. The thicknesses of the second regions 3*s* and 3*t* are greater than the thickness of the first region 3*m*. For this reason, a high contraction stress can be provided to the part around the waist of the disposable wearing article 10*a*.

Figure 9A:
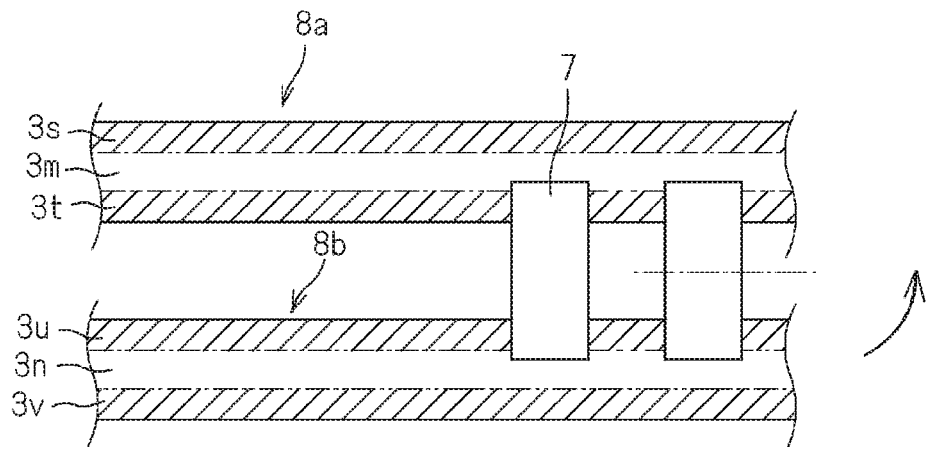
FIGS. 9(a) and 9(b) are explanatory views of a disposable wearing article manufacturing process (third embodiment).
Figure 9B:
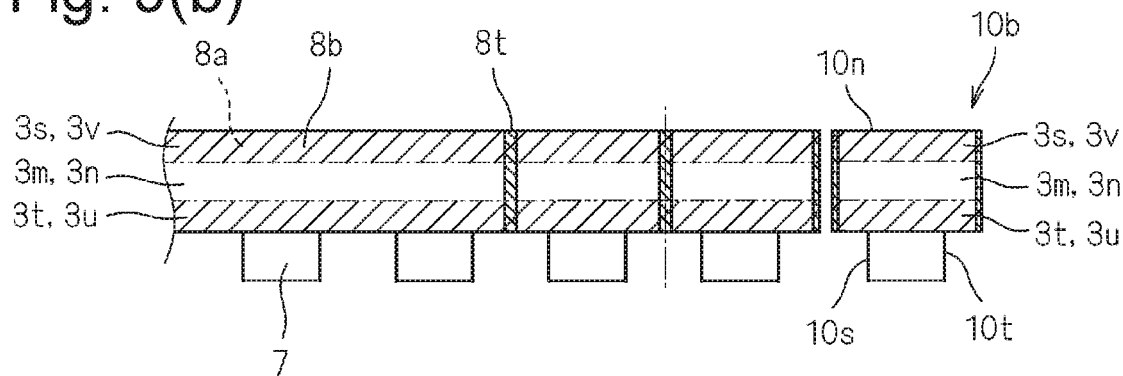
Figure 9B:
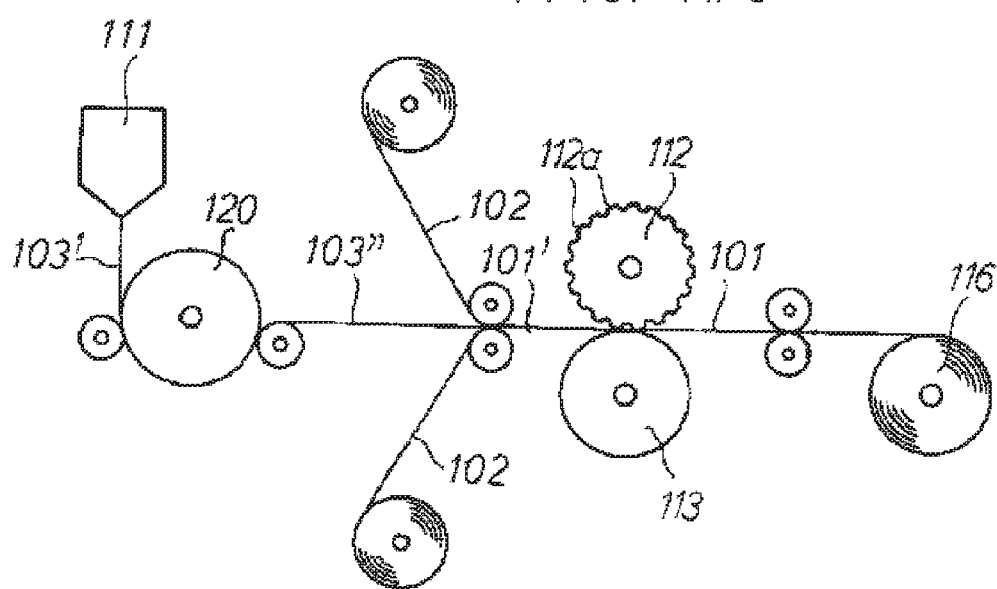

<Third Embodiment> A third embodiment will be described with reference to FIGS. 9(*a*) and 9(*b*). FIGS. 9(*a*) and 9(*b*) are explanatory views of the process for manufacturing a disposable wearing article of the third embodiment.

As shown in FIGS. 9(*a*) and 9(*b*), in the third embodiment, a disposable wearing article 10*b* is manufactured by using two stretchable sheets 8*a* and 8*b* from the beginning instead of dividing one stretchable sheet 8.

First, the first and second stretchable sheets 8*a* and 8*b* are formed as in the second embodiment.

That is, a first elastic resin material having a main component of a first thermoplastic elastic resin which first elastic resin material is heat-melted is extruded into a sheet shape on a first die and made to have a thickness that varies along the width direction, to form a first sheet body including the first region 3*m* in the center in the width direction and the second regions 3*s* and 3*t* on both sides in the width direction, adjoining the first region 3*m* and being greater in thickness than the first region 3*m*; then, the first base sheet is laminated and joined to at least one of the opposing pair of main surfaces of the first sheet body to form the first stretchable sheet 8*a* (first step).

Moreover, a second elastic resin material having a main component of a second thermoplastic elastic resin which second elastic resin material is heat-melted is extruded into a sheet shape on a second die and made to have a thickness that varies along the width direction, to form a second sheet body including a third region 3*n* in the center in the width direction and fourth regions 3*u* and 3*v* on both sides in the width direction, adjoining the third region 3*n* and being greater in thickness than the third region 3*n*; then, the second base sheet is laminated and joined to at least one of the opposing pair of main surfaces of the second sheet body to form the second stretchable sheet 8*b* (second step).

The first thermoplastic elastic resin and the second thermoplastic elastic resin may be either the same or different. When the first and second thermoplastic elastic resins are the same, the first elastic resin material and the second elastic resin material may be either the same or different.

Then, as in the second embodiment, the crotch portions 9 are joined and division into pieces 10*a* is performed.

That is, the first stretchable sheet 8*a* and the second stretchable sheet 8*b* are placed with a predetermined space therebetween (third step).

Then, the crotch portions 9 each including an absorber are disposed at intervals in the length direction of the first stretchable sheet 8*a* and the second stretchable sheet 8*b* so as to lie astride the first stretchable sheet 8*a* and the second stretchable sheet 8*b* placed with a predetermined space therebetween, and joined to the first stretchable sheet 8*a* and the second stretchable sheet 8*b*. The absorber may be added to the crotch portions 9 after the crotch portions 9 are joined to the first and second divisional sheets 8*p* and 8*q* (fourth step).

Then, the first stretchable sheet 8*a* and the second stretchable sheet 8*b* are superposed on each other by folding at the crotch portions 9, and the first stretchable sheet 8*a* and the second stretchable sheet 8*b* are joined together between the adjoining crotch portions 9 to form side seal portions 8*t* (fifth step).

Then, the first stretchable sheet 8*a* and the second stretchable sheet 8*b* are cut at the side seal portions 8*t* to take out the pieces 10*a* (sixth step).

In each divisional piece 10*b*, the first stretchable sheet 8*a* and the second stretchable sheet 8*b* are connected together by a pair of side seal portions 8*t* that are cut. The divisional piece 10*b* is a disposable wearing article 10*b* structured so that an opening 10*n* around the body is formed by the first stretchable sheet 8*a* and the second stretchable sheet 8*b* and a pair of openings 10*s* and 10*t* around the legs are formed by the first stretchable sheet 8*a*, the second stretchable sheet 8*b* and the crotch portion 9. The front body portion and the rear body portion of the disposable wearing article 10*b* are formed by the first and second stretchable sheets 8*a* and 8*b*.

In the disposable wearing article 10*b*, the first and second stretchable sheets 8*a* and 8*b* are disposed so that a portion 3*s* of the second region is closer to the opening 10*n* around the body than the first region 3*m* and that a portion 3*v* of the fourth region is closer to the opening 10*n* around the body than the third region 3*n*. Moreover, they are disposed so that another portion 3*t* of the second region is closer to the openings 10*s* and 10*t* around the legs than the first region 3*m* and that another portion 3*u* of the fourth region is closer to the openings 10*s* and 10*t* around the legs than the third region 3*n*. The thicknesses of the second regions 3*s* and 3*t* are greater than the thickness of the first region 3*m*, and the thicknesses of the fourth regions 3*u* and 3*v* are greater than the thickness of the third region 3*n*. For this reason, a high contraction stress can be provided to the part around the waist and the parts around the legs of the disposable wearing article 10*b*.

<Summary> As described above, a stretchable sheet in which the stretching characteristics vary along the width direction, a disposable wearing article using the stretchable sheet in which the stretching characteristics vary along the width direction, and a method for manufacturing the same can be provided.

The present invention is not limited to the above-described embodiments and may be variously modified when carried out.

For example, a sheet material other than nonwoven fabric may be used as the base sheet.

EXPLANATIONS OF LETTERS OR NUMERALS 2, 2a Intermediate product
2b Laminated body
2p One end side in the width direction
2q The other end side in the width direction
2u, 2v Addition
3 Sheet body
3m First region 3m
3s, 3t Second region
3n Third region
3u, 3v Fourth region
4 First nonwoven fabric (base sheet)
6 Second nonwoven fabric (base sheet)
8, 8a, 8b Stretchable sheet
8p, 8q Divisional sheet
8s, 8t Side seal portion
8x Slit
9 Crotch portion
10, 10a, 10b Piece (disposable wearing article)
10m, 10n Opening around the body
10p, 10q, 10s, 10t Opening around the leg
20 Die
24, 24a Lip
24m, 24s, 24t Part
Wm, Ws, Wt Lip width

The invention claimed is:

1. A stretchable sheet manufacturing method, comprising:
heat-melting an elastic resin material having a main component of a thermoplastic elastic resin,
forming the heat-melted elastic resin material into a sheet shape having a thickness that varies along a width direction by discharging the heat-melted elastic resin material in a sheet form from a lip of a die, the lip of the die being configured to extend in the width direction,
cooling the heat-melted elastic resin material formed into the sheet shape to a temperature range in which the heat-melted elastic resin material elastically deforms, to form a sheet body that varies in thickness along the width direction, and
laminating and joining a base sheet to at least one of opposing main surfaces of the sheet body,
wherein the heat-melted elastic resin material formed into the sheet shape before being cooled consists, in the width direction, of a single center region having an equal thickness and two side regions having thicknesses greater than that of the center region, to thereby have elasticity different in the width direction.

2. The stretchable sheet manufacturing method according to claim 1, wherein an intermediate product made of the heat-melted elastic resin material discharged in the sheet form from the lip of the die is stretched in a uniaxial direction to thereby contract a width of the intermediate product to make a thickness of the intermediate product vary along the width direction, and is then cooled to the temperature range to form the sheet body that varies in thickness along the width direction.

3. The stretchable sheet manufacturing method according to claim 1, wherein the heat-melted elastic resin material is discharged in the sheet form from the lip of the die having a part different in a lip width, to form an intermediate product that is made to vary in thickness along the width direction, and the intermediate product is cooled to the temperature range to form the sheet body that varies in thickness along the width direction.

4. The stretchable sheet manufacturing method according to claim 1, wherein the heat-melted elastic resin material discharged in the sheet form from the lip of the die is stretched until the heat-melted elastic resin material reaches a cooling roller disposed below the lip of the die.

* * * * *